United States Patent
Leimbach et al.

(10) Patent No.: US 9,795,379 B2
(45) Date of Patent: Oct. 24, 2017

(54) SURGICAL INSTRUMENT WITH MULTI-DIAMETER SHAFT

(71) Applicant: Ethicon Endo-Surgery, Inc., Cincinnati, OH (US)

(72) Inventors: Richard L. Leimbach, Cincinnati, OH (US); Ryan J. Laurent, Loveland, OH (US); Jeffrey C. Gagel, Loveland, OH (US); Nicholas Fanelli, Morrow, OH (US); Jason E. Zerkle, Blanchester, OH (US)

(73) Assignee: Ethicon LLC, Guaynabo, PR (US)

( * ) Notice: Subject to any disclaimer, the term of this patent is extended or adjusted under 35 U.S.C. 154(b) by 834 days.

(21) Appl. No.: 13/780,402

(22) Filed: Feb. 28, 2013

(65) Prior Publication Data

US 2014/0239038 A1 Aug. 28, 2014

(51) Int. Cl.
*A61B 17/00* (2006.01)
*A61B 17/068* (2006.01)
*A61B 17/072* (2006.01)
*A61B 17/29* (2006.01)

(52) U.S. Cl.
CPC ...... *A61B 17/068* (2013.01); *A61B 17/07207* (2013.01); *A61B 2017/00398* (2013.01); *A61B 2017/00734* (2013.01); *A61B 2017/07228* (2013.01); *A61B 2017/07257* (2013.01); *A61B 2017/07285* (2013.01); *A61B 2017/2927* (2013.01); *A61B 2017/2946* (2013.01)

(58) Field of Classification Search
CPC .............................................. A61B 2017/2927
USPC ..................................................... 227/175.1
See application file for complete search history.

(56) References Cited

U.S. PATENT DOCUMENTS

| | | | |
|---|---|---|---|
| 4,805,823 A | 2/1989 | Rothfuss | |
| 5,275,323 A | 1/1994 | Schulze et al. | |
| 5,307,976 A | 5/1994 | Olson et al. | |
| 5,415,334 A | 5/1995 | Williamson, IV et al. | |
| 5,456,401 A * | 10/1995 | Green .............. | A61B 17/07207 227/176.1 |

(Continued)

FOREIGN PATENT DOCUMENTS

EP   2 140 819 A1   1/2010

OTHER PUBLICATIONS

U.S. Appl. No. 13/780,067, filed Feb. 28, 2013, Fanelli et al.

(Continued)

*Primary Examiner* — Andrew M Tecco
*Assistant Examiner* — Chelsea Stinson
(74) *Attorney, Agent, or Firm* — Frost Brown Todd LLC

(57) ABSTRACT

An apparatus includes an end effector and a shaft having a longitudinal axis. The end effector includes a first jaw and second jaw. The first jaw is pivotable relative to the second jaw. The distal end of the shaft has an articulation joint that pivots the end effector from a first position aligned with the longitudinal axis of the shaft to a second position angled from the longitudinal axis of the shaft. The articulation joint includes at least one articulation band that bends outwardly within the shaft when the end effector is in the first position. The articulation band then bends inwardly when the end effector is pivoted from the first position to the second position. The shaft includes an outer closure tube having a neck-down region that promotes a greater range of pivotal movement within a surgical passageway.

20 Claims, 18 Drawing Sheets

(56) References Cited

U.S. PATENT DOCUMENTS

| | | | |
|---|---|---|---|
| 5,465,895 A | 11/1995 | Knodel et al. | |
| 5,553,765 A | 9/1996 | Knodel et al. | |
| 5,562,241 A | 10/1996 | Knodel et al. | |
| 5,597,107 A | 1/1997 | Knodel et al. | |
| 5,632,432 A | 5/1997 | Schulze et al. | |
| 5,662,258 A | 9/1997 | Knodel et al. | |
| 5,662,667 A | 9/1997 | Knodel | |
| 5,669,544 A | 9/1997 | Schulze | |
| 5,673,840 A | 10/1997 | Schulze et al. | |
| 5,673,841 A | 10/1997 | Schulze et al. | |
| 5,680,982 A | 10/1997 | Schulze et al. | |
| 5,692,668 A | 12/1997 | Schulze et al. | |
| 5,704,534 A * | 1/1998 | Huitema | A61B 17/07207 227/175.1 |
| 5,713,505 A * | 2/1998 | Huitema | A61B 17/07207 227/175.1 |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,569,105 B1 * | 5/2003 | Kortenbach | A61B 10/06 600/562 |
| 6,666,854 B1 * | 12/2003 | Lange | A61B 17/2909 606/1 |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,111,769 B2 * | 9/2006 | Wales | A61B 17/07207 227/175.1 |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 * | 6/2008 | Shelton, IV | A61B 17/0686 227/175.1 |
| 7,404,508 B2 | 7/2008 | Smith et al. | |
| 7,434,715 B2 | 10/2008 | Shelton, IV et al. | |
| 7,441,684 B2 * | 10/2008 | Shelton, IV | A61B 17/068 227/175.1 |
| 7,506,790 B2 * | 3/2009 | Shelton, IV | A61B 17/07207 227/175.1 |
| 7,524,320 B2 | 4/2009 | Tierney et al. | |
| 7,559,450 B2 | 7/2009 | Wales et al. | |
| 7,644,848 B2 | 1/2010 | Swayze et al. | |
| 7,690,547 B2 | 4/2010 | Racenet et al. | |
| 7,691,098 B2 | 4/2010 | Wallace et al. | |
| 7,703,653 B2 | 4/2010 | Shah et al. | |
| 7,721,930 B2 | 5/2010 | McKenna et al. | |
| 7,806,891 B2 | 10/2010 | Nowlin et al. | |
| 8,210,411 B2 | 7/2012 | Yates et al. | |
| 8,282,543 B2 * | 10/2012 | Ishiguro | A61B 17/29 600/104 |
| 8,357,161 B2 * | 1/2013 | Mueller | A61B 17/29 606/205 |
| 8,490,851 B2 | 7/2013 | Blier et al. | |
| 8,783,541 B2 | 7/2014 | Shelton, IV et al. | |
| 9,038,880 B1 * | 5/2015 | Donohoe | A61B 1/00064 227/175.1 |
| 9,101,358 B2 * | 8/2015 | Kerr | A61B 17/07207 |
| 9,138,226 B2 | 9/2015 | Racenet et al. | |
| 9,220,559 B2 * | 12/2015 | Worrell | A61B 18/1445 |
| 2005/0165415 A1 * | 7/2005 | Wales | A61B 17/07207 606/139 |
| 2007/0221701 A1 * | 9/2007 | Ortiz | A61B 17/068 227/175.1 |
| 2008/0029574 A1 * | 2/2008 | Shelton | A61B 17/07207 227/175.2 |
| 2010/0022837 A1 * | 1/2010 | Ishiguro | A61B 17/29 600/127 |
| 2010/0264193 A1 | 10/2010 | Huang et al. | |
| 2011/0106078 A1 * | 5/2011 | Mueller | A61B 17/29 606/52 |
| 2012/0080482 A1 * | 4/2012 | Schall | A61B 17/00234 227/176.1 |
| 2012/0132450 A1 | 5/2012 | Timm et al. | |
| 2012/0138660 A1 | 6/2012 | Shelton, IV | |
| 2012/0199630 A1 | 8/2012 | Shelton, IV | |
| 2012/0199631 A1 | 8/2012 | Shelton, IV et al. | |
| 2012/0199632 A1 | 8/2012 | Spivey et al. | |
| 2012/0199633 A1 | 8/2012 | Shelton, IV et al. | |
| 2012/0205421 A1 | 8/2012 | Shelton, IV | |
| 2012/0211546 A1 | 8/2012 | Shelton, IV | |
| 2012/0239012 A1 | 9/2012 | Laurent et al. | |
| 2013/0012957 A1 | 1/2013 | Shelton, IV et al. | |
| 2014/0243801 A1 * | 8/2014 | Fanelli | A61B 17/07207 606/1 |

OTHER PUBLICATIONS

U.S. Appl. No. 13/780,082, filed Feb. 28, 2013, Zerkle et al.
U.S. Appl. No. 13/780,106, filed Feb. 28, 2013, Simms et al.
U.S. Appl. No. 13/780,120, filed Feb. 28, 2013, Zerkle et al.
U.S. Appl. No. 13/780,162, filed Feb. 28, 2013, Fanelli et al.
U.S. Appl. No. 13/780,379, filed Feb. 28, 2013, Boudreaux et al.
U.S. Appl. No. 13/780,417, filed Feb. 28, 2013, Hoffman.
European Search Report and Written Opinion dated Jun. 18, 2014 for Application No. EP 14157357.6, 8 pgs.
International Search Report and Written Opinion dated May 27, 2014 for Application No. PCT/US2014/017329, 11 pgs.

* cited by examiner

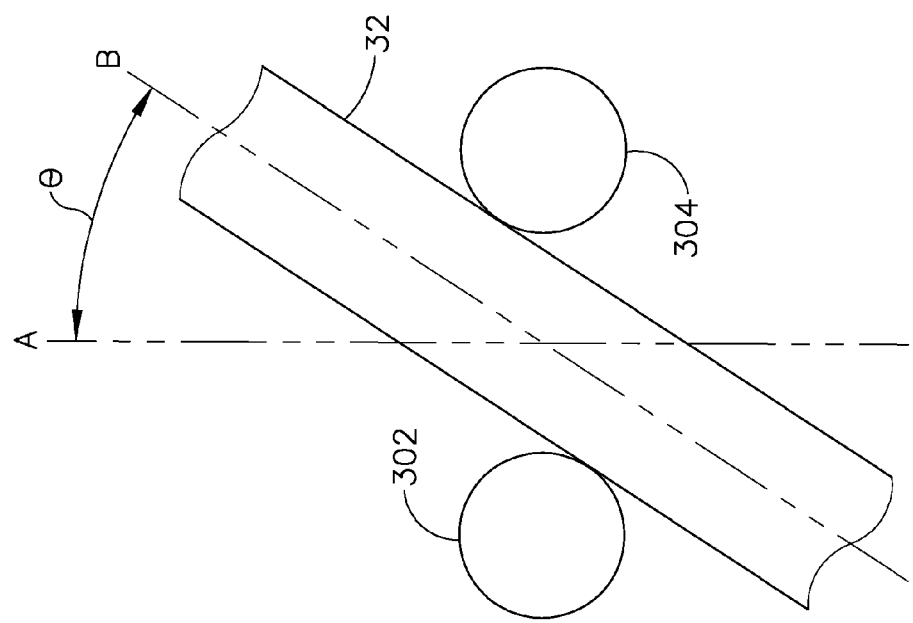
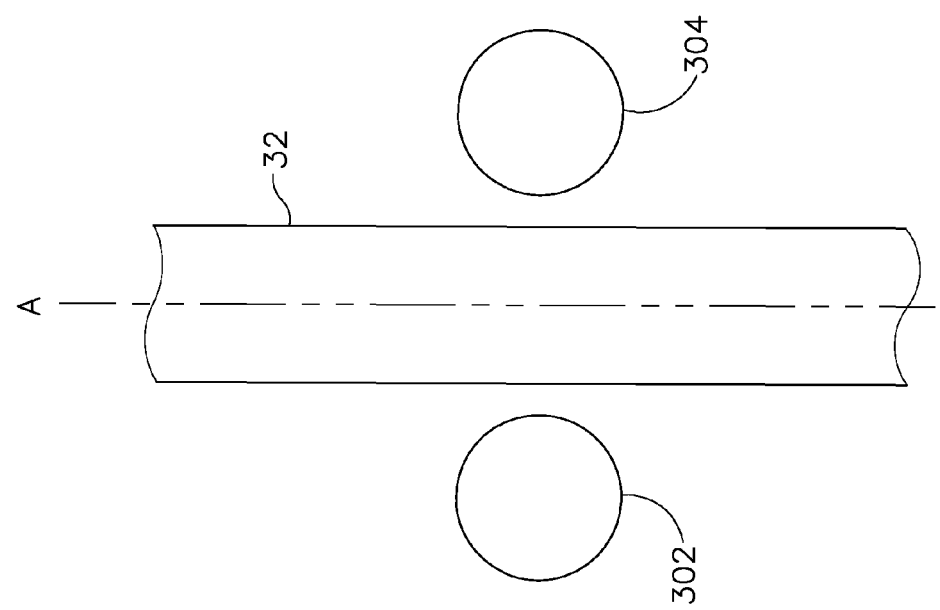

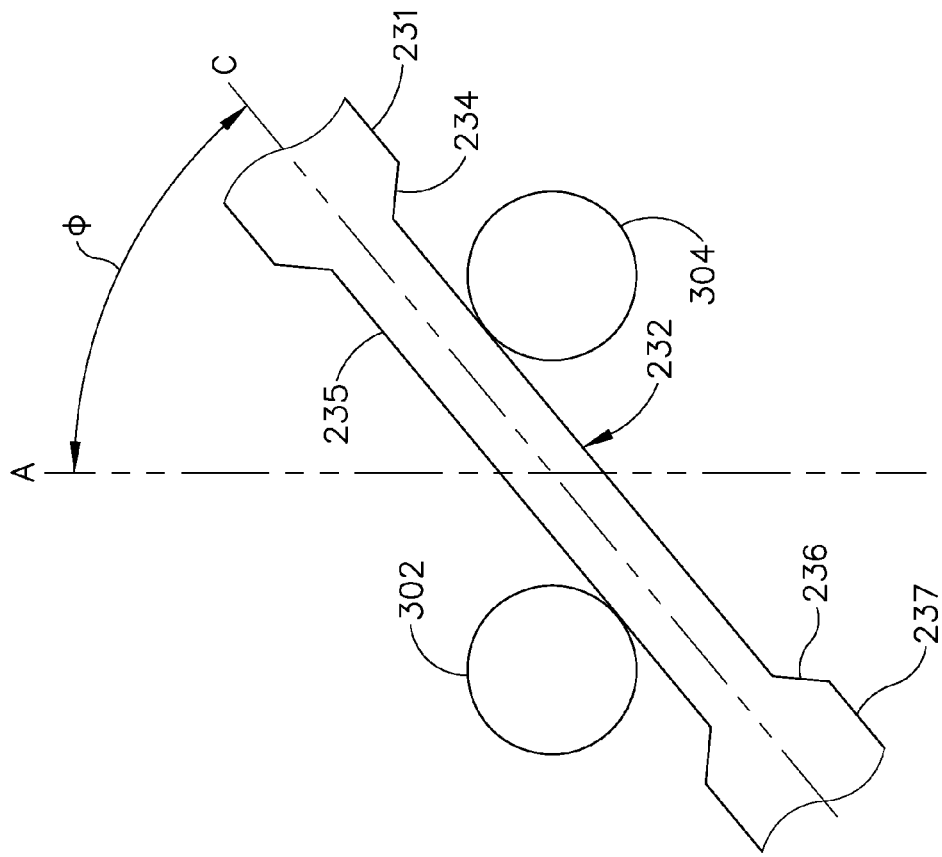
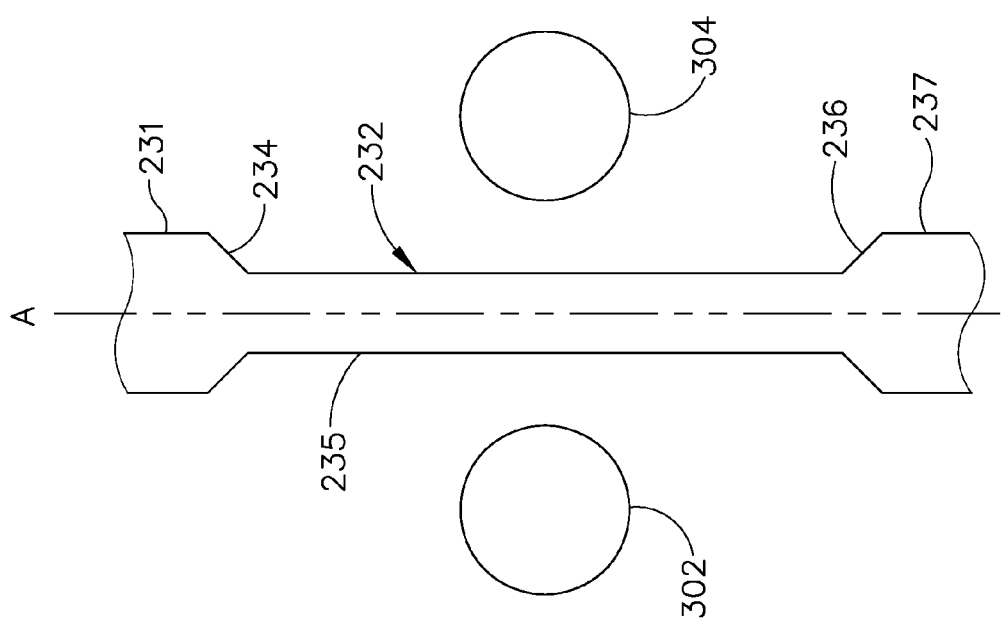

SURGICAL INSTRUMENT WITH MULTI-DIAMETER SHAFT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued Apr. 2, 2013 as U.S. Pat. No. 8,408,439; and U.S. Pub. No. 2012/0239012, entitled "Motor-Driven Surgical Cutting Instrument with Electric Actuator Directional Control Assembly," published Sep. 20, 2012, issued Jun. 4, 2013 as U.S. Pat. No. 8,453,914. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 14A depicts a schematic of the shaft of the instrument of FIG. 1 inserted between two ribs;

FIG. 14B depicts a schematic of the shaft of the instrument of FIG. 1 pivoted between two ribs;

FIG. 15A depicts a schematic of the shaft of the instrument of FIG. 12 inserted between two ribs;

FIG. 15B depicts a schematic of the shaft of the instrument of FIG. 12 pivoted between two ribs;

Figure 1:
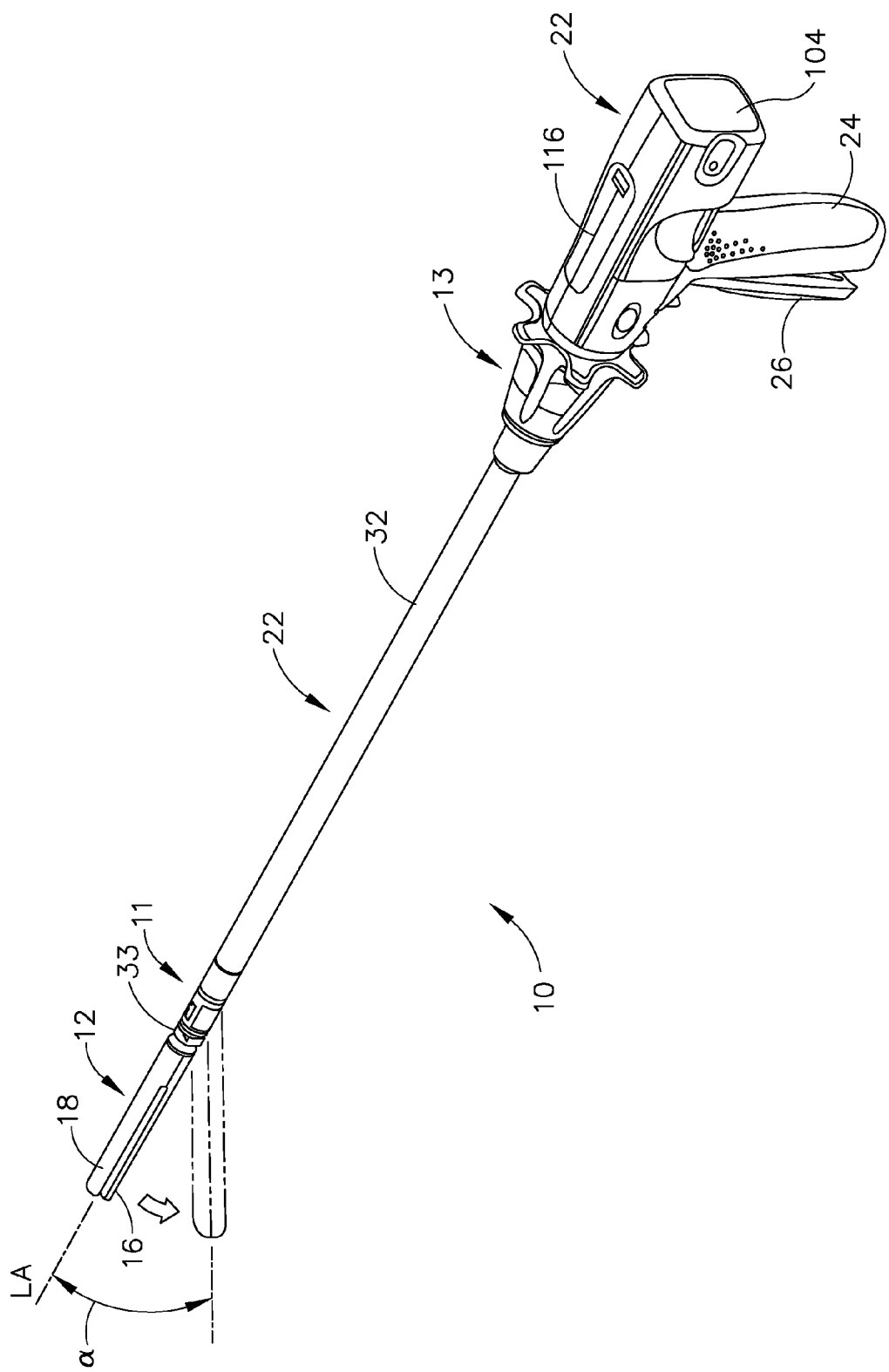
FIG. 1 depicts a perspective view of an exemplary articulating surgical stapling instrument.
Figure 2:
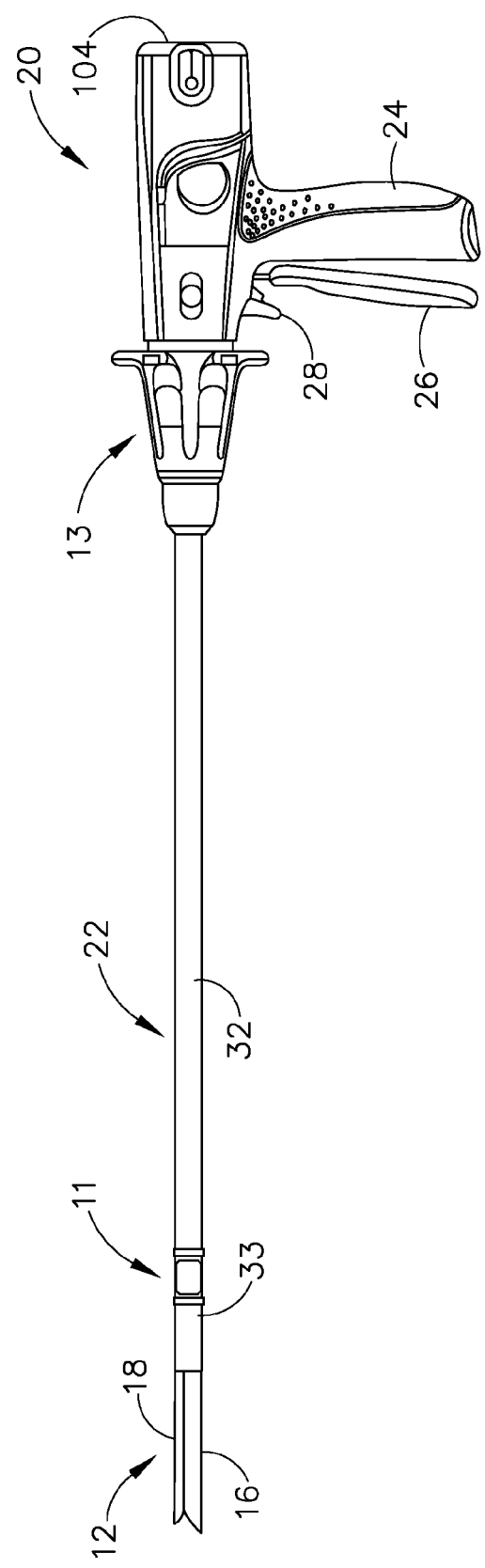
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). Various suitable features, configurations, and operabilities for shaft (22) will be described in greater detail below. Other suitable configurations for shaft (22) will be apparent to those of ordinary skill in the art in view of the teachings herein. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067 entitled "Surgical Instrument End Effector Articulation Drive with Pinion and Opposing Racks," filed on even date herewith, now U.S. Pat. No. 9,186,142, issued on Nov. 17, 2015, the disclosure of which is incorporated by reference herein. Articulation joint (11) may also be constructed and operable in accordance with the various teachings below. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417, entitled "Installation Features for Surgical Instrument End Effector Cartridge," filed on even date herewith, published as U.S. Pub. No. 2014/0239044 on Aug. 28, 2014, the disclosure of which is incorporated by reference herein. Anvil (18) may be constructed in accordance with at least some of the teachings of U.S. patent application Ser. No. 13/780,106, entitled "Integrated Tissue Positioning and Jaw Alignment Features for Surgical Stapler," filed on even date herewith, now U.S. Pat. No. 9,517,065, issued on Dec. 13, 2016, the disclosure of which is incorporated by reference herein; at least some of the teachings of U.S. patent application Ser. No. 13/780,120, entitled "Jaw Closure Feature for End Effector of Surgical Instrument," filed on even date herewith, published as U.S. Pub. No. 2014/0239036 on Feb. 28, 2014, the disclosure of which is incorporated by reference herein; and/or at least some of the teachings of U.S. patent application Ser. No. 13/780,379, entitled "Staple Forming Features for Surgical Stapling Instrument," filed on even date herewith, published as U.S. Pub. No. 2014/0239037 on Aug. 28, 2014, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082, entitled "Lockout Feature for Movable Cutting Member of Surgical Instrument," filed on even date herewith, now U.S. Pat. No. 9,717,497, issued on Aug. 1, 2017, the disclosure of which is incorporated by reference herein. Other suitable forms that firing beam (14) may take will be apparent to those of ordinary skill in the art in view of the teachings herein.

Figure 3:
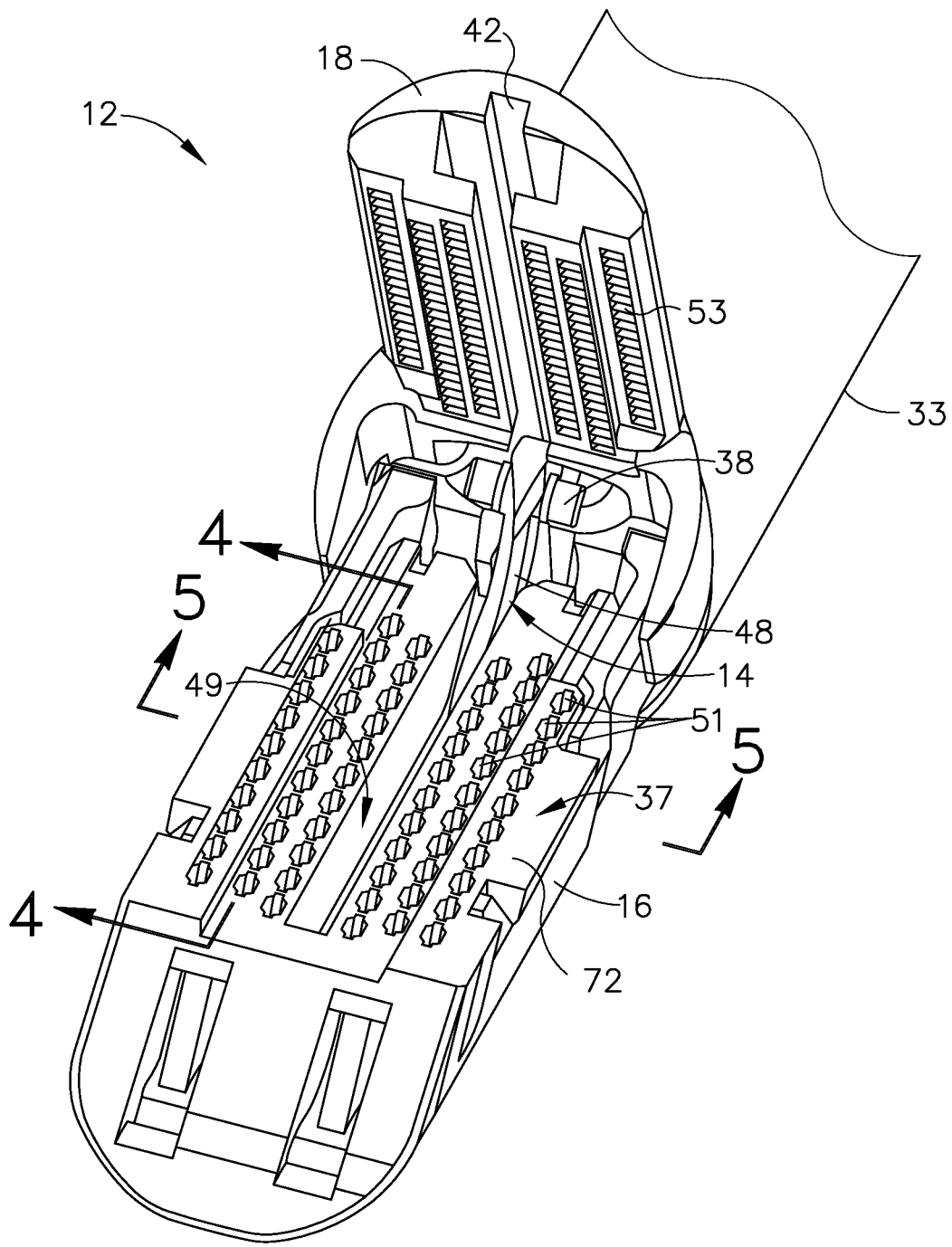
FIG. 3 depicts a perspective view of an opened end effector of the instrument of FIG. 1.
Figure 4A:
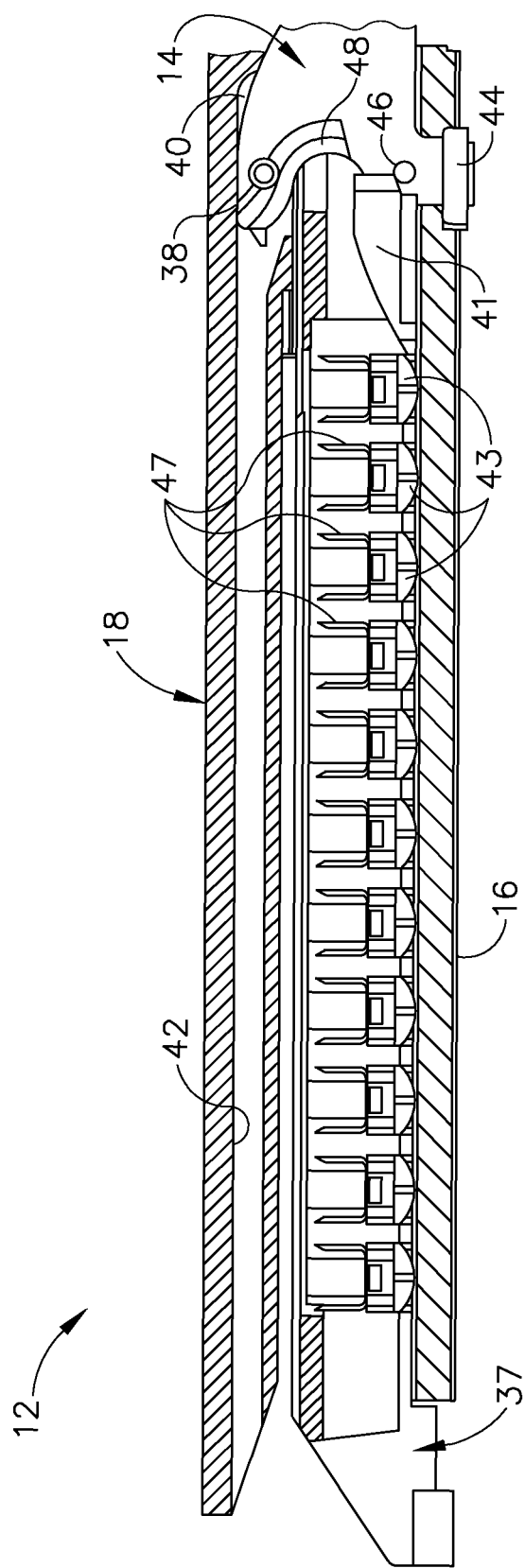
FIG. 4A depicts a side cross-sectional view of the end effector of FIG. 3, taken along line 4-4 of FIG. 3, with the firing beam in a proximal position.
Figure 4B:
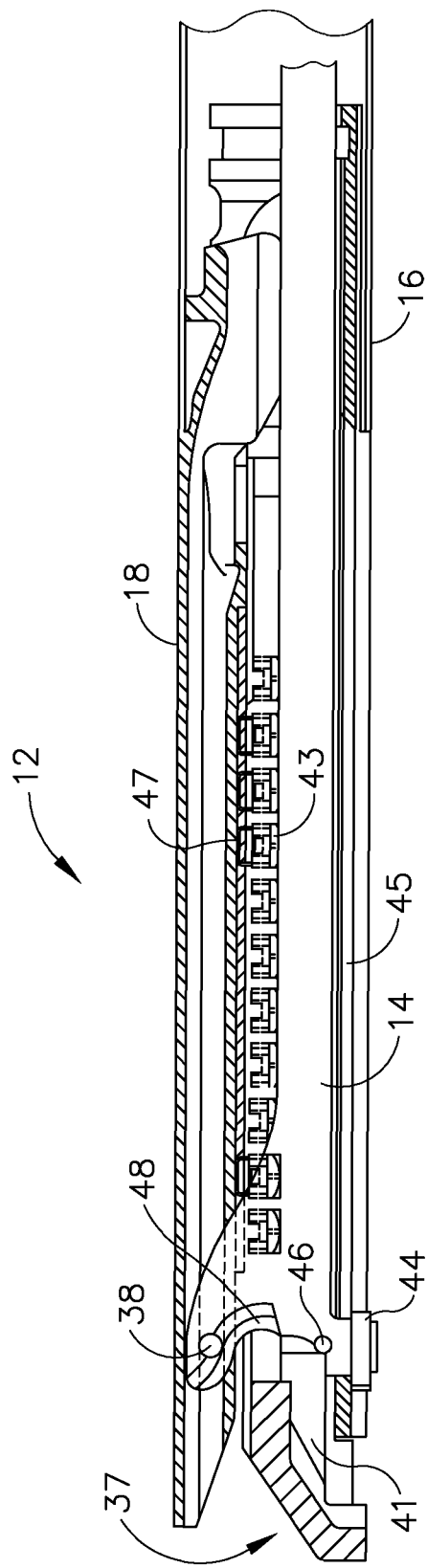
FIG. 4B depicts a side cross-sectional view of the end effector of FIG. 3, taken along line 4-4 of FIG. 3, with the firing beam in a distal position.
Figure 5:
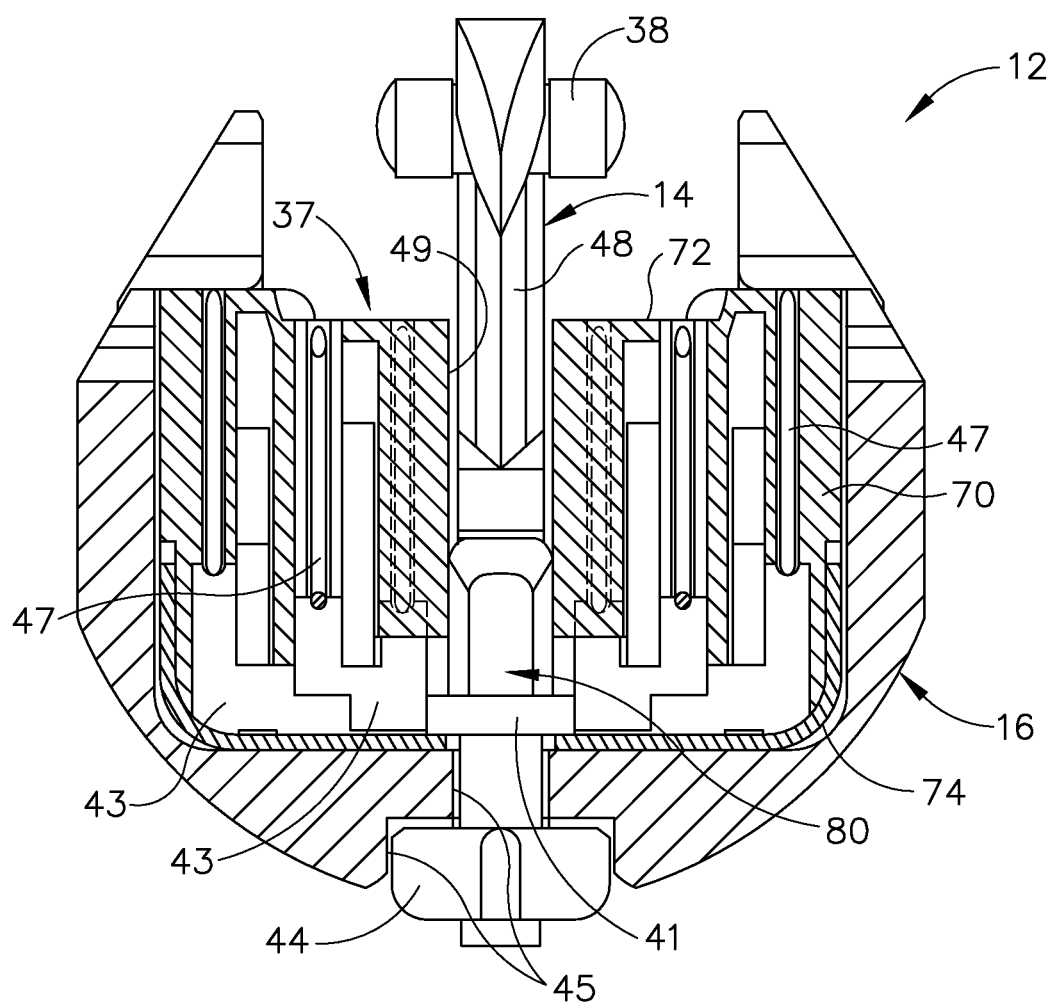
FIG. 5 depicts an end cross-sectional view of the end effector of FIG. 3, taken along line 5-5 of FIG. 3.
Figure 6:
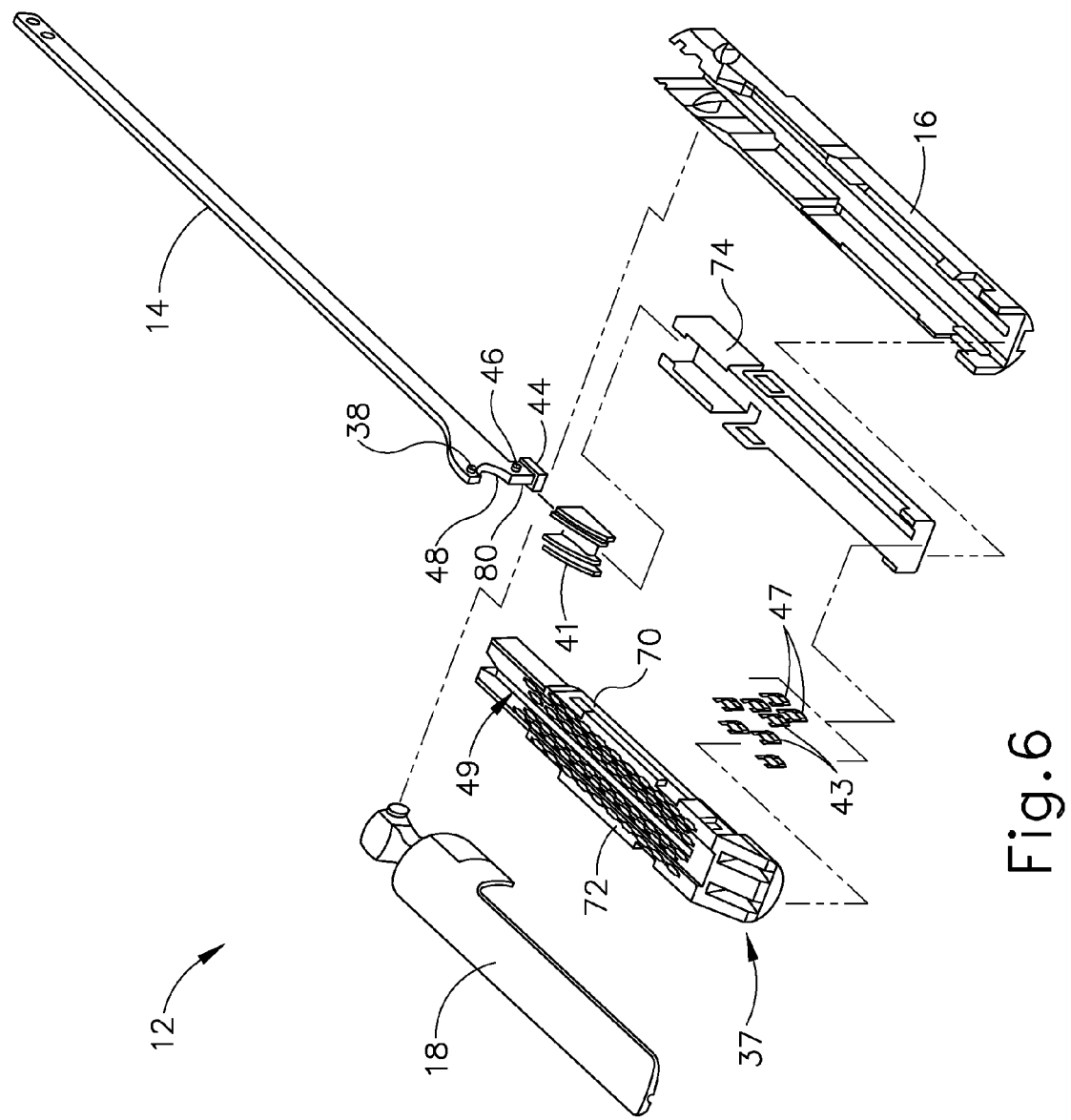
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, now U.S. Pat. No. 9,517,065, issued on Dec. 13, 2016, the disclosure of which is incorporated by reference herein. In addition or in the alternative, staple cartridge (37) may be constructed and operable in accordance with at least some of the teachings of U.S. patent application Ser. No. 13/780,417, published as U.S. Pub. No. 2014/0239044 on Aug. 28, 2014, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
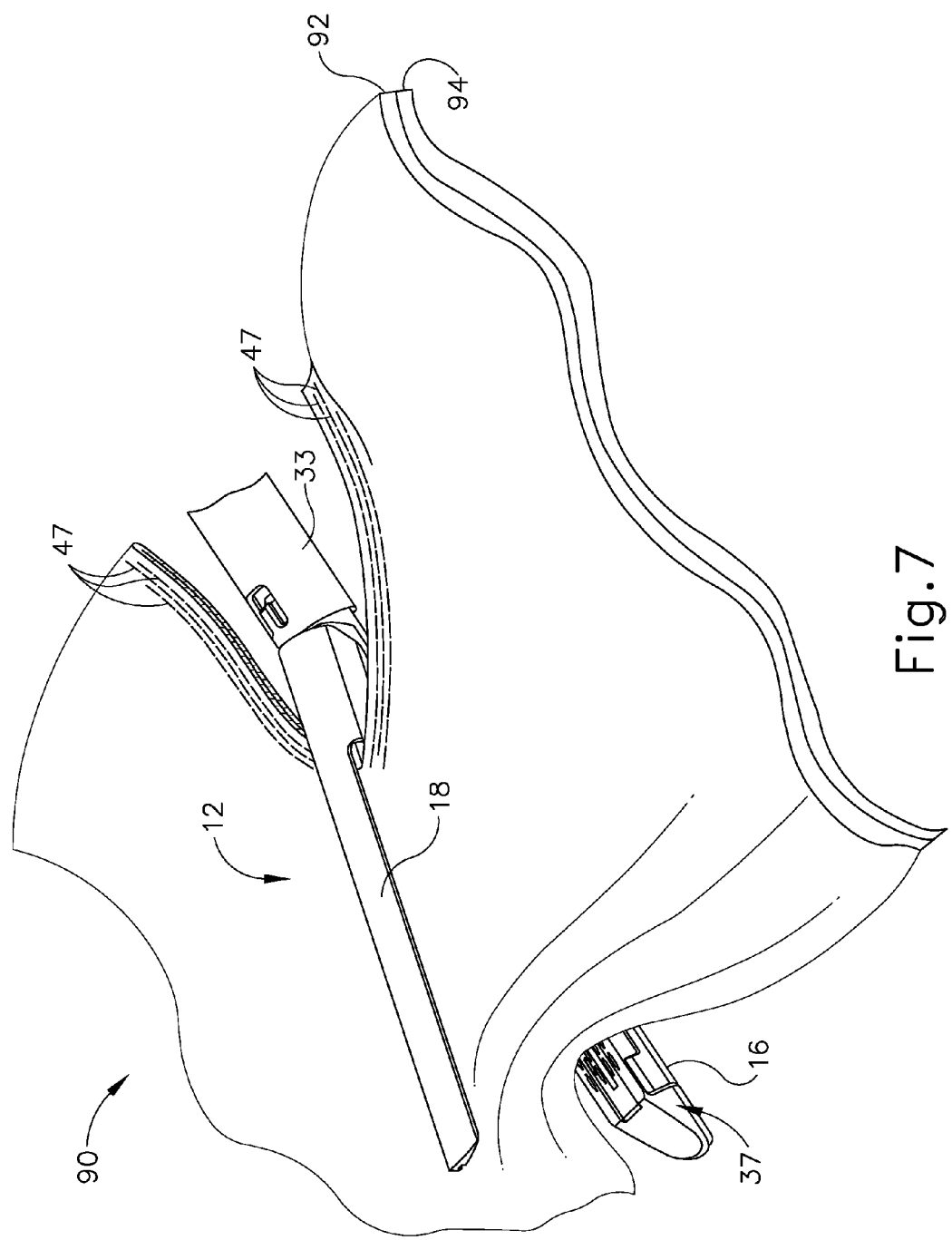
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193, issued as U.S. Pat. No. 8,408,439; and/or 2012/0239012, issued as U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
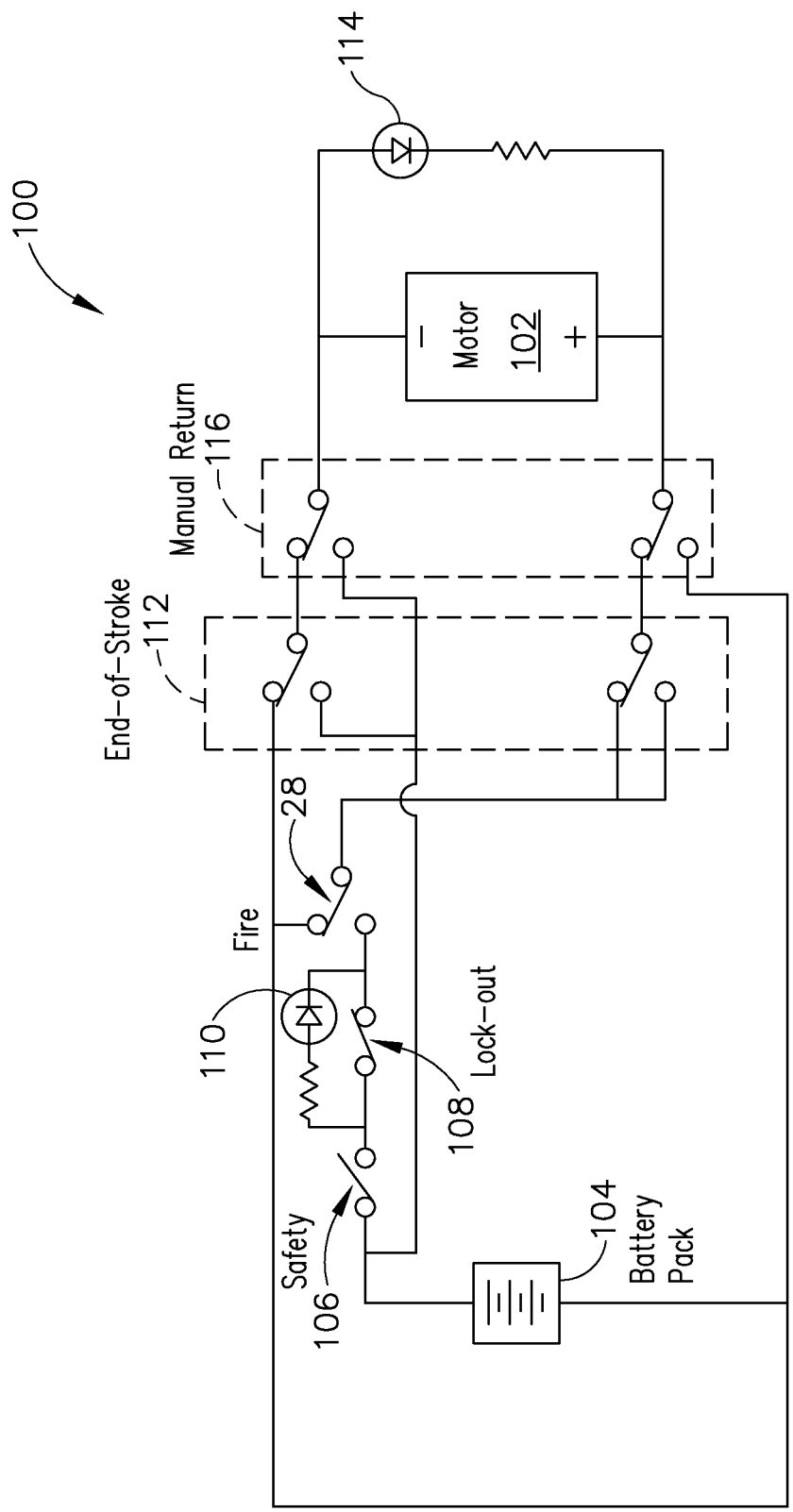
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
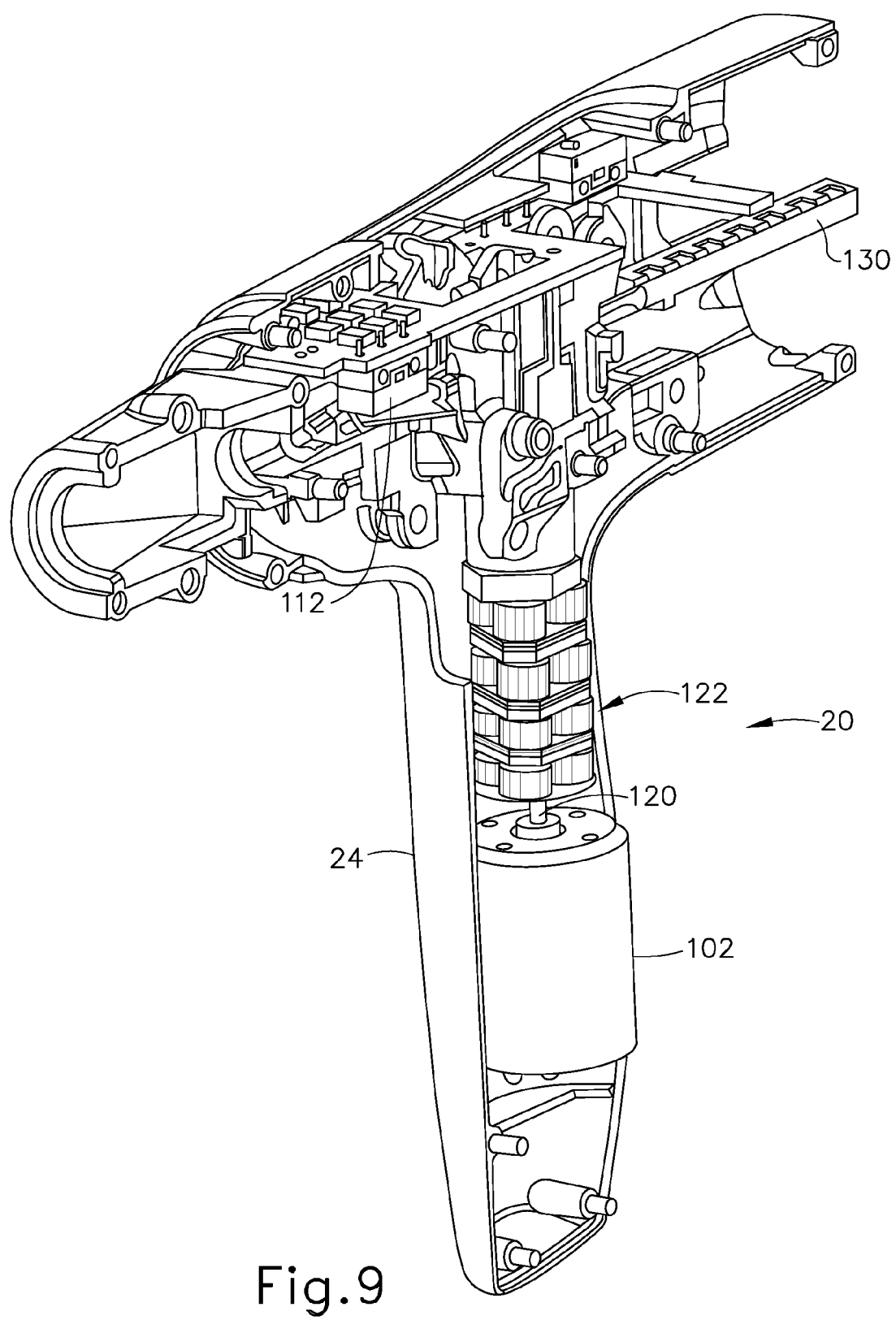
FIG. 9 depicts a perspective view of the handle assembly of the instrument of FIG. 1, with a housing half removed.
Figure 10:
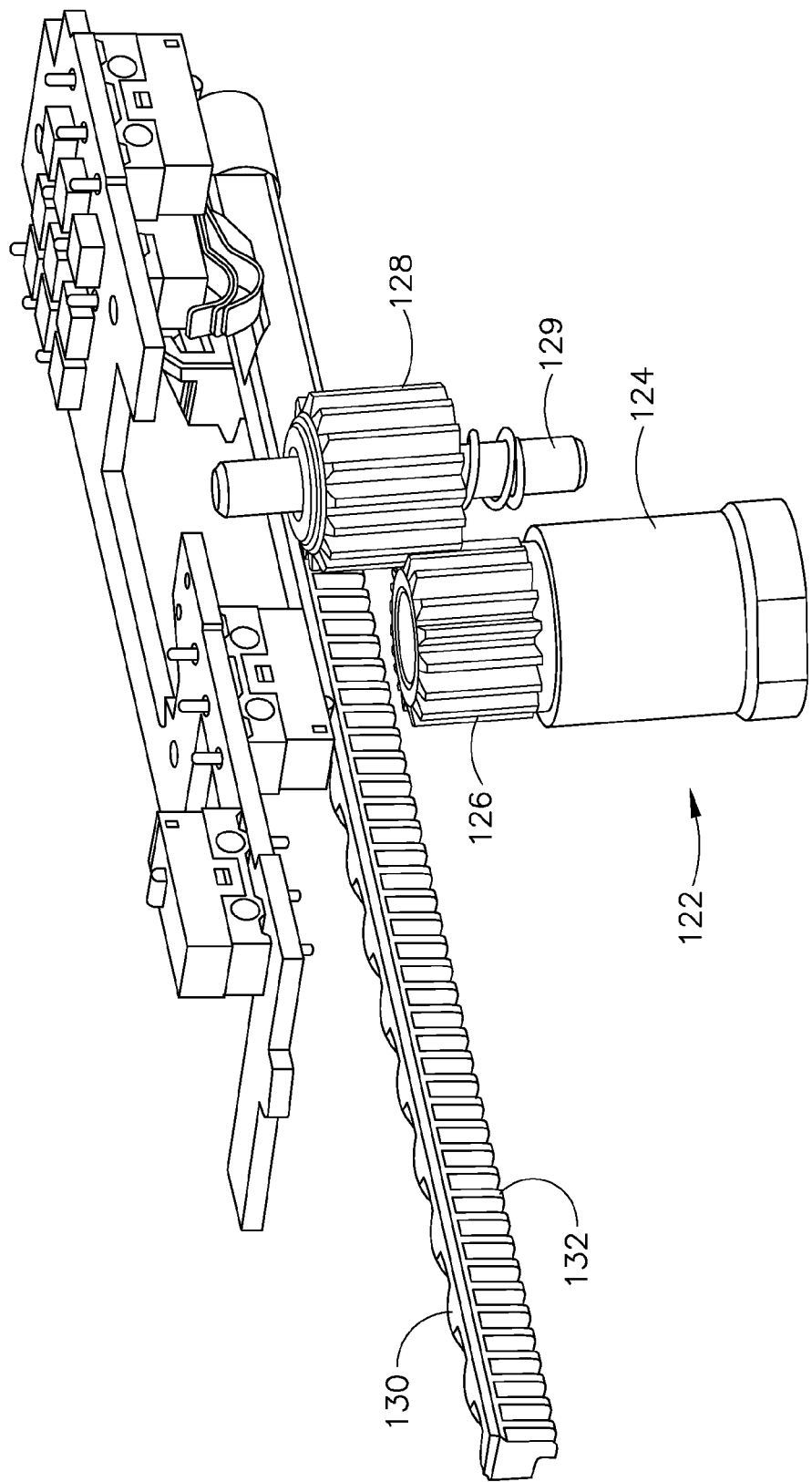
FIG. 10 depicts a perspective view of drive assembly components from the handle assembly of FIG. 9.
Figure 11:
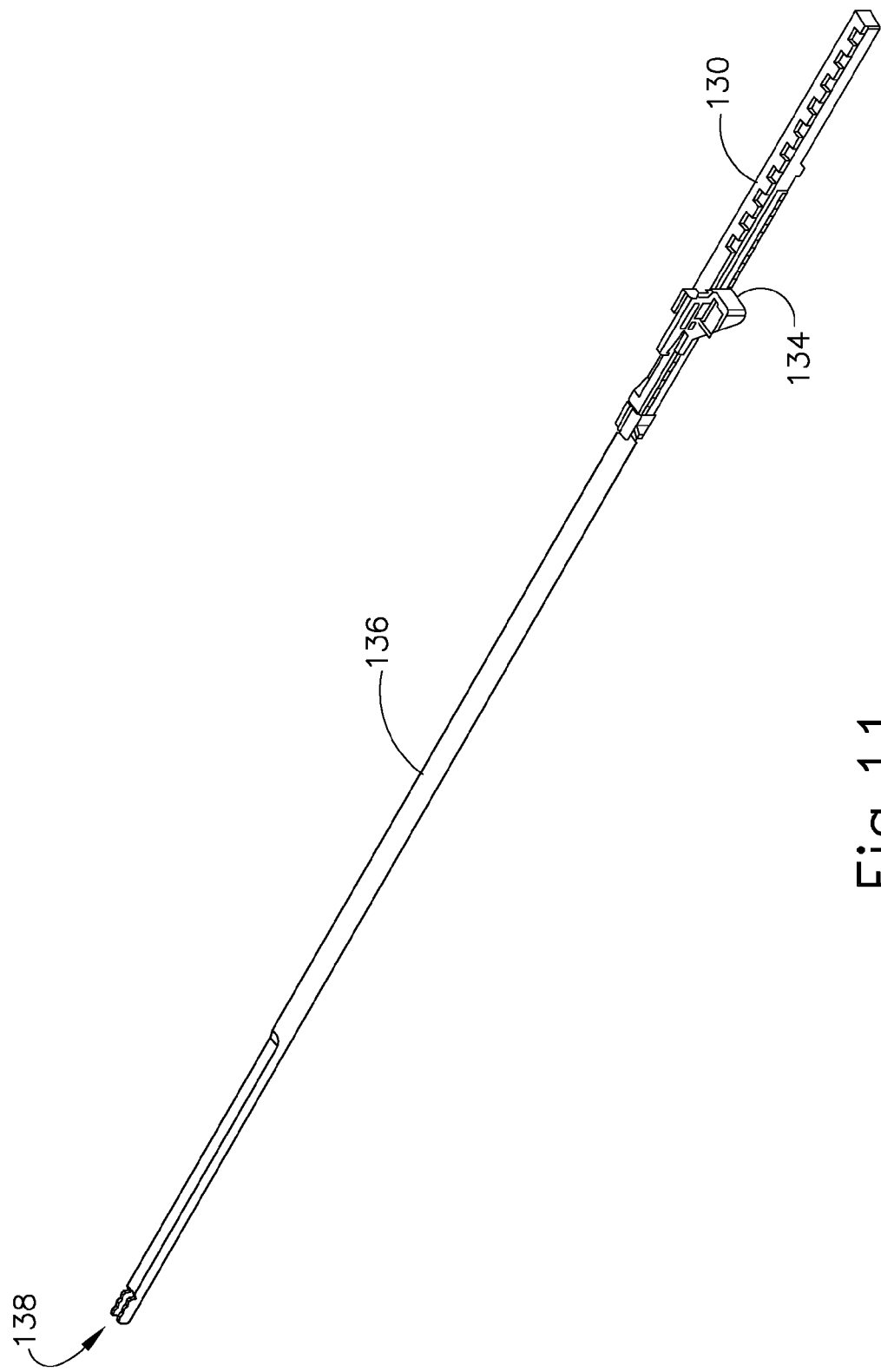
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012, issued as U.S. Pat. No. 8,453,914, the disclosure of which is incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary Multi-Diameter Shaft Surgical Instrument

In some instances, it may be desirable to increase the amount of movement and positioning ability of instrument (10). For example, instrument (10) may be inserted through a trocar or thoracotomy such that shaft (22) is positioned between a patient's ribs or elsewhere. It may be desirable to angle or move shaft (22) without prying or otherwise damaging the patient's ribs or soft tissue around the thoracotomy. Accordingly, instrument (10) may include multi-diameter shaft features that allows for increased movement or positioning ability of instrument (10). The examples below include several merely illustrative versions of multi-diameter shaft features that may be readily introduced to a surgical instrument (10).

Figure 12:
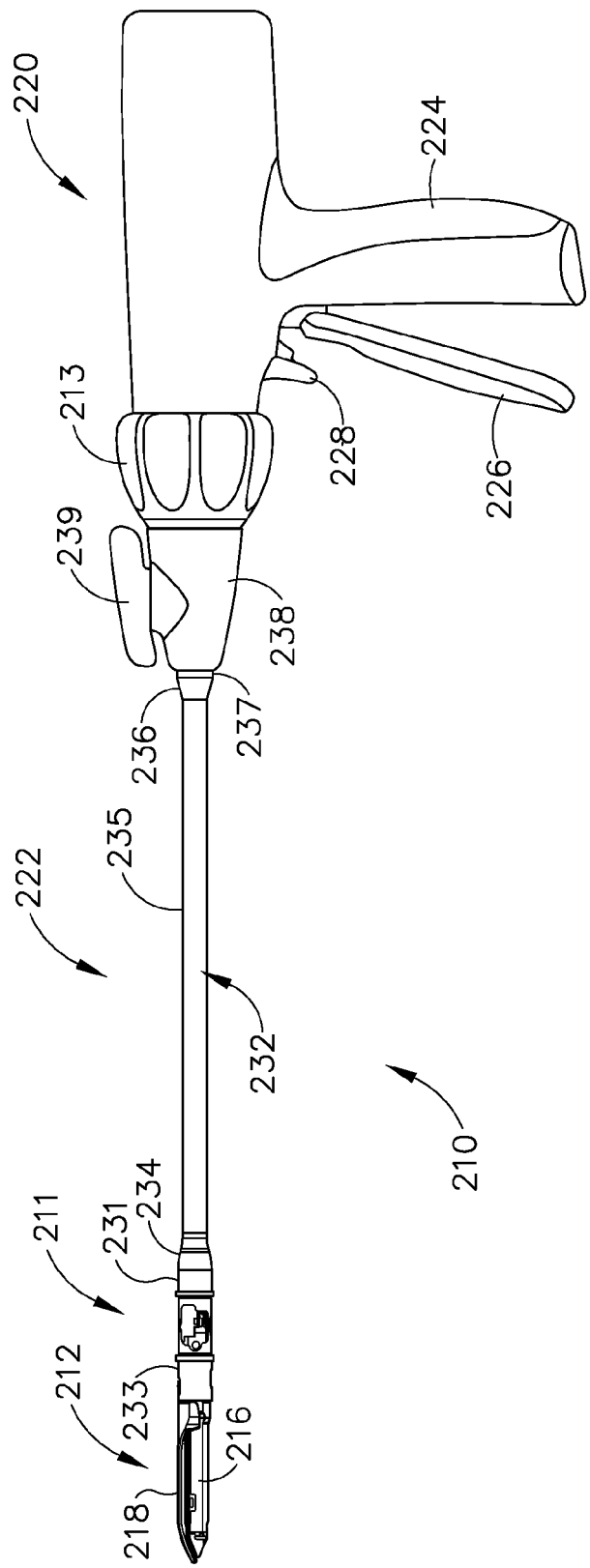
FIG. 12 depicts a side view of another exemplary articulating surgical stapling instrument.

FIG. 12 shows an exemplary surgical instrument (210) that includes multi-diameter shaft features. Instrument (210) is similar to instrument (10), except as otherwise described below. Instrument (210) of the present example comprises a handle portion (220) coupled to an end effector (212) via shaft (222). End effector (212) is similar to end effector (12) and comprises a lower jaw (216) and a pivotable anvil (218). Handle portion (220) is similar to handle portion (20) and comprises a pistol grip (224) and a closure trigger (226). Closure trigger (226) is pivotable toward pistol grip (224) to cause clamping, or closing, of the anvil (218) toward lower jaw (216) of end effector (212). Firing trigger (228) of handle portion (220) may be actuated to translate a firing beam distally to cause the stapling and severing of clamped tissue in end effector (212). Thereafter, triggers (226, 228) may be released to release the tissue from end effector (212).

Handle portion (220) further comprises a rotation knob (213) and a control knob (239). Rotation knob (213) may be rotated to rotate shaft (222) and end effector (212) about the longitudinal axis of shaft (222) and relative to handle portion (220) such that end effector (212) may be positioned at different rotational positions about the longitudinal axis of shaft (222) within the patient. Control knob (239) extends from handle portion (220) and may be rotated to deflect end effector (212) from the longitudinal axis of shaft (222) at articulation joint (211), which will be discussed in greater detail below. Instrument (210) may interface with a person, robotic controller, or other drive method apparent to one with ordinary skill in the art in view of the teachings herein.

A. Exemplary Shaft

Figure 13:
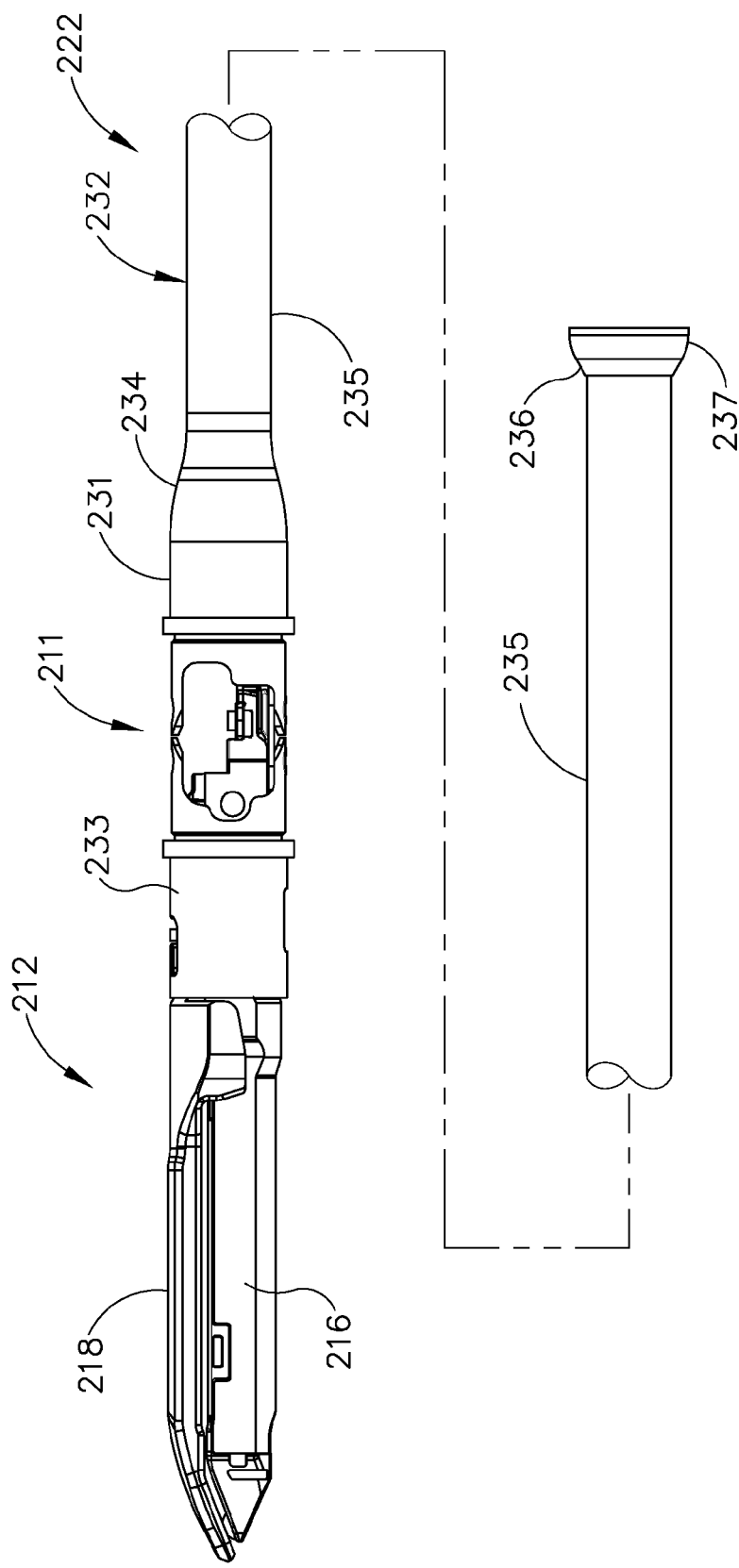
FIG. 13 depicts a side view of an end effector and shaft of the instrument of FIG. 12.

FIG. 13 shows shaft (222) in more detail. Shaft (222) is similar to shaft (22), except that shaft (222) comprises a closure tube (232) having portions (231, 234, 235, 236, 237) with varying diameters. Distal portion (231) is positioned distal on closure tube (232) and is sized to couple to articulation joint (211). Ramped distal portion (234) is connected with and proximal to distal portion (231); and has a diameter that gradually decreases in the proximal direction. Central portion (235) is proximally connected with ramped distal portion (234). Central portion (235) of closure tube (232) has a substantially constant diameter that is smaller than the diameter of distal portion (231) and is configured to be positioned within a thoracotomy, between a pair of ribs, within a trocar, etc. The decreased diameter of central portion (235) of closure tube (232) allows for increased movement and positioning of end effector (212) without prying ribs or otherwise damaging soft tissue around the thoracotomy. The diameter of central portion (235) may be about 70% of the diameter of distal portion (231). Of course, any of a number of other combinations of sizes of central portions (235) may be provided. The transition between the diameters of distal portion (231) and central portion (235) provided by ramped distal portion (234) may reduce patient trauma and prevent seal inversion if instrument (210) is used with a trocar. Ramped proximal portion (236) is proximally connected with central portion (235) of closure tube (232) and has a diameter that gradually increases in the proximal direction. Proximal portion (237) of closure tube (232) is proximally connected with ramped proximal portion (236) and is sized to couple with distal portion (238) of handle portion (220). Proximal portion (237) has a larger diameter than central portion (235). Portions (231, 234, 235, 236, 237) of closure tube (232) may be formed from a single piece or multiple pieces of shaft (222). Shaft (222) may be manufactured by manual expansion, hydroforming, tube welding, or other suitable processes apparent to one with ordinary skill in the art in view of the teachings herein.

Closure tube (232) may be driven distally by pivoting closure trigger (226) toward pistol grip (224). Closure tube (232) is coupled with closure ring (233), such that closure ring (233) translates distally when closure tube (232) translates distally. Closure ring (233) then drives anvil (218) to pivot toward lower jaw (216) when closure ring (233) translates distally, to thereby clamp tissue positioned between jaws (216, 218).

As described above, shaft (222) may be positioned within a thoracotomy, between a pair of ribs, a trocar, etc. to increase movement and positioning of end effector (212) as compared to movement and positioning permitted by shaft (32). As shown in FIG. 14A, closure tube (32) of shaft (22) is inserted between a pair of ribs (302, 304). Closure tube (32) defines a longitudinal axis (A) that is perpendicular to ribs (302, 304) at insertion. Closure tube (32) is then angled to position end effector (12) within the patient. As shown in FIG. 14B, closure tube (32) is angled until closure tube (32) contacts each rib (302, 304). Closure tube (32) defines a longitudinal axis (B) in this position. The angle between longitudinal axis (A) and longitudinal axis (B) is the maximum pivot angle (θ-THETA) that closure tube (32) may travel to position end effector (12) until closure tube (32) contacts ribs (302, 304). FIGS. 15A-15B show central portion (235) of closure tube (232) of shaft (222) positioned between a pair of ribs (302, 304). Closure tube (232) is inserted perpendicularly between ribs (302, 304) at the same longitudinal axis (A) as closure tube (32), as shown in FIG. 15A. Closure tube (232) is then pivoted to position end effector (212) until closure tube (232) contacts ribs (302, 304). Closure tube (232) defines longitudinal axis (C) at this position. The angle between longitudinal axis (A) and longitudinal axis (C) is the maximum pivot angle (Φ-PHI) that closure tube (232) may travel to position end effector (212) until closure tube (232) contacts ribs (302, 304). Because central portion (235) of closure tube (232) has a smaller diameter than closure tube (32), closure tube (232) has a larger maximum pivot angle (Φ-PHI) than the maximum pivot angle (θ-THETA) of closure tube (32). This enables closure tube (232) to increase the range of movement and positioning of end effector (212).

B. Exemplary Articulation Joint

As described above with respect to FIG. 12, shaft (222) distally terminates in an articulation joint (211), which is further coupled to end effector (212). Articulation joint (211) may be remotely articulated by control knob (239) such that end effector (212) may be deflected from the longitudinal axis (LA) of shaft (222) at a desired angle (a), similar to end effector (12) as shown in FIG. 1. End effector (212) may thereby reach behind an organ or approach tissue from a desired angle or for other reasons. In some versions, articulation joint (211) enables deflection of end effector (212) along a single plane. In some other versions, articulation joint (211) enables deflection of end effector along more than one plane. Articulation joint (211) and control knob (239) may be configured in accordance with the teachings of any of the numerous references that are cited herein. By way of example only, some merely illustrative alternative examples of articulation joint (211) and control knob (239) are disclosed in U.S. patent application Ser. No. 13/780,067, now U.S. Pat. No. 9,186,142, issued on Nov. 17, 2015, the disclosure of which is incorporated by reference herein. Alternatively, articulation joint (211) and/or control knob (239) may have any other suitable configurations.

Figure 16A:
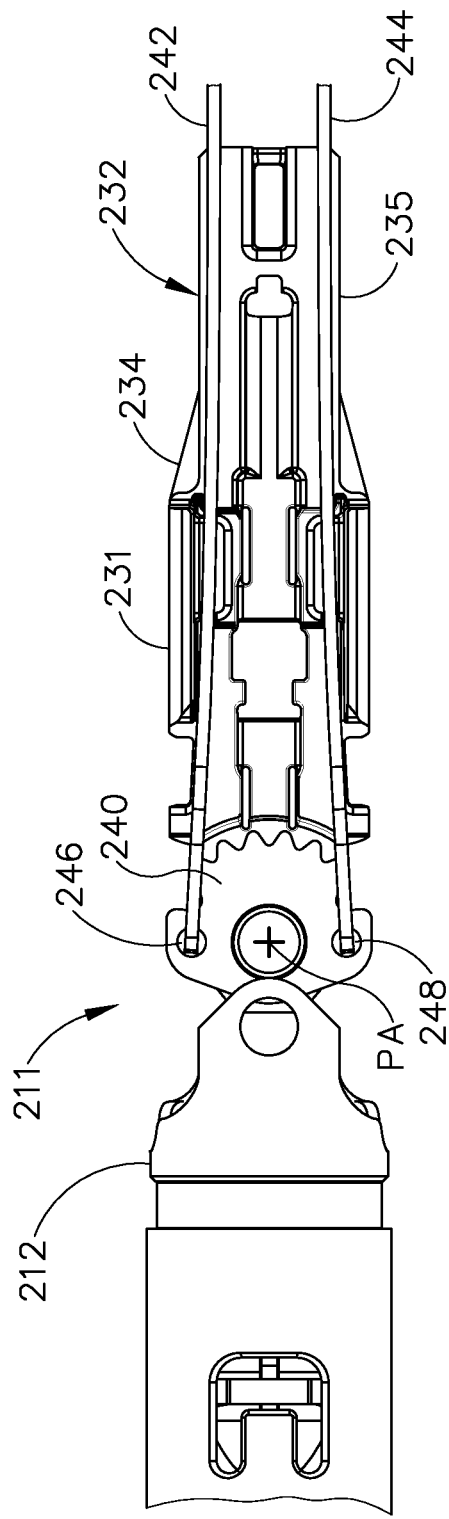
FIG. 16A depicts a cross sectional top view of an articulation joint of the instrument of FIG. 12 in an non-articulated configuration.
Figure 16B:
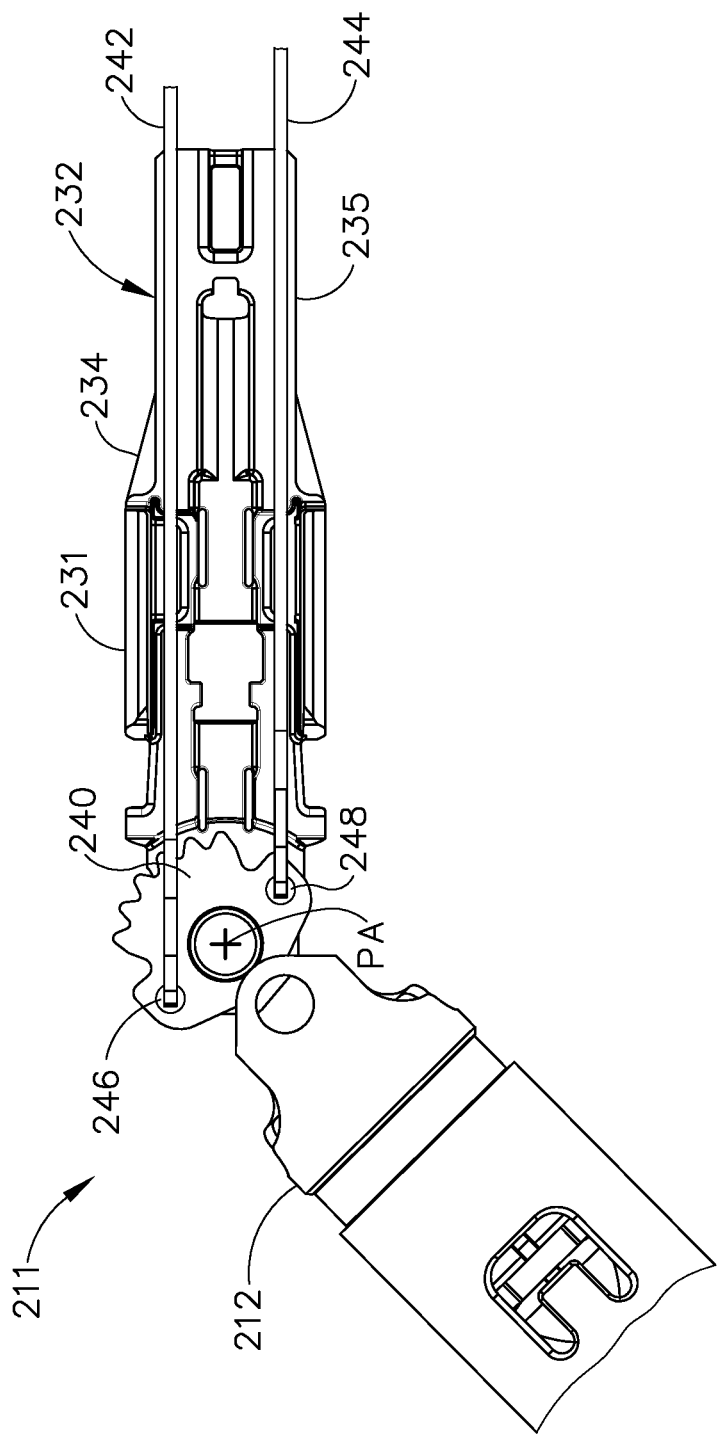
FIG. 16B depicts a cross sectional top view of the articulation joint of FIG. 16A in an articulated configuration.

FIGS. 16A-16B show articulation joint (211) of the present example in greater detail. It should be understood that several components of articulation joint (211) are omitted from FIGS. 16A-16B for clarity. Such omitted components may be configured and operable in accordance with at least some of the teachings of U.S. patent application Ser. No. 13/780,067, now U.S. Pat. No. 9,186,142, issued on Nov. 17, 2015, the disclosure of which is incorporated by reference herein. Articulation joint (211) comprises an articulation gear (240) and articulation bands (242, 244). Gear (240) is coupled with the distal end of closure tube (231) of shaft (222). Gear (240) comprises openings (246, 248) on each side portion of gear (240). The distal end of gear (240) is coupled with end effector (212). Gear (240) is configured to rotate about pivot axis (PA) to position end effector (212) at the desired articulation angle (a). Articulation bands (242, 244) travel the length of shaft (222) such that the proximal ends of bands (242, 244) couple to control knob (239). The distal end of bands (242, 244) couple to gear (240) through openings (246, 248). In the present example, band (242) is coupled with opening (246) and band (244) is coupled with opening (248). FIG. 16A shows articulation joint (211) and end effector (212) in a nonarticulated position such that end effector (212) is longitudinally aligned with shaft (222). When articulation joint (211) and end effector (212) are in the nonarticulated position, openings (246, 248) are positioned to cause bands (242, 244) to flare outwardly in the lateral direction as bands (242, 244) pass through closure tube (232) to gear (240).

FIG. 16B shows articulation joint (211) and end effector (212) in an articulated position such that end effector (212) is deflected at an oblique angle relative to the longitudinal axis of shaft (222). To articulate end effector (212), control knob (239) is rotated. Rotation of control knob (239) is converted into longitudinal translation of at least one articulation band (242, 244) travelling through shaft (222). For instance, control knob (239) may pull one of bands (242, 244) proximally when control knob (239) is rotated, or control knob (239) may pull one of bands (242, 244) proximally and actively push the other of bands (242, 244) distally when control knob (239) is rotated. The at least one band (242, 244) then rotates gear (240) of articulation joint (211) and end effector (212) to the desired angle (a). In the present example, gear (240) is rotated counterclockwise such that opening (246) translated distally, while opening (248) translated proximally. Of course, gear (240) may also be rotated in the clockwise direction. The translation of openings (246, 248) cause bands (242, 244) to flare inwardly in the lateral direction. In the present example, bands (242, 244) are parallel as bands (242, 244) extend through shaft (222). Bands (242, 244) may flare inward when end effector (212) is articulated to articulation angles (a) of about +/−50 degrees. This allows bands (242, 244) to interface with gear (240) while also not impeding on the cross sectional area of structural components positioned adjacent and within bands (242, 244). Bands (242, 244) are made from a compliant material to allow bands (242, 244) to flare inwardly and/or outwardly as articulation joint (211) is actuated, while having sufficient strength to drive articulation of end effector (212) without yielding or buckling. The flaring ability of articulation bands (242, 244) may allow shaft (222) to have a smaller diameter at closure tube (232), increase the maximum articulation angle (a), and/or allow for more robust inner components of instrument (210). While bands (242, 244) are made from a compliant material in the present example, other versions of bands (242, 244) may be formed of a rigid material. For instance, each band (242, 244) may be formed by rigid segments that are joined by pivots, living hinges, or other features that enable the distal ends of bands (242, 244) to flare substantially as described herein.

The teeth of gear (240) may selectively engage a locking member to provide selective locking of articulation angle (α). By way of example only, some merely illustrative alternative examples of locking members are disclosed in U.S. patent application Ser. No. 13/780,067, now U.S. Pat. No. 9,186,142, issued on Nov. 17, 2015, the disclosure of which is incorporated by reference herein; and in U.S. patent application Ser. No. 13/780,162, entitled "Surgical Instrument with Articulation Lock Having a Detenting Binary Spring," filed on even date herewith, published as U.S. Pub. No. 2014/0239040 on Aug. 28, 2014, the disclosure of which is incorporated by reference herein.

C. Exemplary Operation

In an exemplary use, instrument (210) may be inserted to a surgical site in a nonarticulated state with jaws (216, 218) of end effector (212) in the closed position. In the nonarticulated state, end effector (212) is longitudinally aligned with shaft (222) such that articulation bands (242, 244) are flared outward, as shown in FIG. 16A. When instrument (210) is inserted to the surgical site, articulation joint (211) and end effector (212) may be inserted through the cannula passageway of a trocar, or through a thoracotomy, to position central portion (235) of closure tube (232) within the passageway or thoracotomy. Once closure tube (232) is positioned, closure tube (232) may be pivoted to position end effector (212) at a desired surgical site within the patient. For instance, closure tube (232) may be pivoted to a desired pivot angle (Φ-PHI), as shown in FIGS. 15A-15B. Rotation knob (213) may be actuated to rotate end effector (212) relative to handle portion (220) to orient jaws (216, 218) at a desired angular orientation about the longitudinal axis of shaft (222). Articulation joint (211) may then be actuated to deflect end effector (212) to a desired articulation angle (a) to better position end effector (212) within the patient.

To actuate articulation joint (211), control knob (239) may be actuated. The rotation of control knob (239) is converted to opposing longitudinal translation of bands (242, 244). Bands (242, 244) then rotate gear (240) of articulation joint (240), as shown in FIG. 16B. The rotation of gear (240) causes the distal ends of bands (242, 244) to deflect inwardly from the flared position within shaft (222) and to pivot end effector (212) to position end effector (212) at the desired articulation angle (a). In some instances, the distal portions of bands (242, 244) are parallel when end effector (212) is articulated to a particular degree. In some instances, the distal portions of at least one band (242, 244) may even deflect inwardly past parallel when end effector (212) is further articulated. Once end effector (212) is articulated to a desired location, closure trigger (226) may then be actuated toward pistol grip (224) to cause the closing of anvil (218) toward lower jaw (216). Such closing of anvil is provided through closure tube (232) and closure ring (233), which longitudinally translate relative to handle portion (220) in response to pivoting of closure trigger (226) relative to pistol grip (224). Once end effector (212) is closed, the tissue captured between anvil (218) and lower jaw (216) may be cut and stapled by actuating firing trigger (228).

To open end effector (212), closure trigger (226) may be released away from pistol grip (224) to translate closure tube (232) and closure ring (233) proximally and pivot anvil (218) away from lower jaw (216). End effector (212) may then be returned to the nonarticulated position. Control knob (239) may be rotated such that at least one of bands (242, 244) translate to rotate gear (240) of articulation joint (211) and longitudinally align end effector (212) with shaft (222), as shown in FIG. 16A. When end effector (212) is returned to the nonarticulated position, bands (242, 244) return to the outward flared position. With instrument (210) in the nonarticulated position and end effector jaws (216, 218) in the open position, staple cartridge (37) may be replaced with a new staple cartridge such that instrument (210) may cut and/or staple additional tissue. Alternatively, closure trigger (226) may again be actuated to close jaws (216, 218) of end effector (212). Instrument (210) may then be removed from the surgical site. Staple cartridge (37) may then be replaced with a new staple cartridge, and end effector (212) may be again inserted to the surgical site for further cutting and stapling.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued Dec. 31, 2013 as U.S. Pat. No. 8,616,431, the disclosure of which is incorporated by reference herein; U.S. Pub. No. 2012/0199633, entitled "Surgical Stapling Instruments with Cam-Driven Staple Deployment Arrangements," published Aug. 9, 2012, issued Nov. 5, 2013 as U.S. Pat. No. 8,573,461, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued Dec. 10, 2013 as U.S. Pat. No. 8,602,288, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued on Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued Jul. 9, 2013 as U.S. Pat. No. 8,479,969; U.S. Pub. No. 2012/0138660, entitled "Robotically-Controlled Cable-Based Surgical End Effectors," published Jun. 7, 2012, now U.S. Pat. No. 8,800,838, issued on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued Nov. 5, 2013 as U.S. Pat. No. 8,573,465, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an end effector, wherein the end effector comprises a first jaw and a second jaw, wherein the first jaw is movable relative to the second jaw; and
   (b) a shaft having a longitudinal axis, wherein a distal end of the shaft comprises:
      (i) an articulation joint coupled with the end effector, wherein the articulation joint is operable to pivot the end effector from a first position where the end effector is aligned with the longitudinal axis of the shaft to a second position where the end effector is angled relative to the longitudinal axis of the shaft, and
      (ii) at least one articulation band, wherein a distal end of the articulation band is configured to bend outwardly to a flared position within the shaft when the end effector is in the first position, wherein a portion of the distal end of the articulation band is connected to the articulation joint, wherein the distal end of the articulation band is configured to form an oblique angle with the longitudinal axis when the distal end of the articulation band is in the flared position, wherein the distal end of the articulation band is configured to bend inwardly from the flared position within the shaft during a transition of end effector between the first position and the second position.

2. The apparatus of claim 1, wherein the end effector is configured to pivot from the second position to the first position, wherein the distal end of the articulation band is configured to bend outwardly when the end effector is pivoted from the second position to the first position.

3. The apparatus of claim 1, wherein the articulation band is compliant.

4. The apparatus of claim 1, wherein the distal end of the articulation band is coupled with a rotational member, wherein the rotational member is operable to pivot the end effector when the rotational member is rotated.

5. The apparatus of claim 1, further comprising a body, wherein a proximal end of the shaft is coupled with the body, wherein the articulation band extends through the shaft such that a proximal end of the articulation band is coupled with the body.

6. The apparatus of claim 5, wherein the body comprises a first actuator, wherein the proximal end of the articulation band is coupled with the first actuator such that the first actuator is operable to pivot the end effector via the articulation band.

7. The apparatus of claim 6, wherein the body comprises a second actuator, wherein the second actuator is operable to rotate the shaft and the end effector about the longitudinal axis of the shaft relative to the body.

8. The apparatus of claim 1, wherein the end effector is pivotable at least about 50 degrees from the longitudinal axis of the shaft.

9. The apparatus of claim 1, wherein the articulation joint comprises two articulation bands.

10. The apparatus of claim 1, wherein the shaft comprises a first outer diameter, wherein the shaft comprises a second outer diameter proximal of the first outer diameter, wherein the second outer diameter is smaller than the first outer diameter.

11. The apparatus of claim 10, wherein the first outer diameter corresponds to an outer diameter of the articulation joint.

12. The apparatus of claim 10, wherein the second outer diameter is about 70% of the first outer diameter.

13. The apparatus of claim 10, wherein the shaft gradually slopes from the first outer diameter to the second outer diameter.

14. The apparatus of claim 10, wherein the shaft comprises a third outer diameter proximal of the second outer diameter, wherein the third outer diameter is larger than the second outer diameter.

15. The apparatus of claim 14, wherein the shaft gradually slopes from the second outer diameter to the third outer diameter.

16. The apparatus of claim 1, wherein the end effector is configured to staple tissue between the first and second jaws of the end effector.

17. An apparatus comprising:
   (a) a body;
   (b) an end effector, wherein the end effector comprises a first jaw and a second jaw, wherein the first jaw is pivotable relative to the second jaw; and
   (c) a shaft coupling the body with the end effector, wherein the shaft comprises an articulation joint, wherein the articulation joint is operable to pivot the end effector from a first position aligned with a longitudinal axis of the shaft to a second position angled from the longitudinal axis of the shaft, wherein the articulation joint comprises a pair of articulation bands, wherein the articulation bands are configured to translate in opposing directions to pivot the end effector from the first position to the second position, wherein the articulation bands are configured to both bend inwardly or both bend outwardly relative to the longitudinal axis of the shaft while translating in opposing directions, such that at least a portion of each articulation band is configured to move in a symmetrically opposing transverse motion relative to the longitudinal axis of the shaft while the articulation bands translate in opposing longitudinal directions.

18. An apparatus comprising:
   (a) a body;
   (b) an end effector, wherein the end effector comprises a first jaw and a second jaw, wherein the first jaw is movable relative to the second jaw; and
   (c) a shaft coupling the body with the end effector, wherein the shaft comprises a pair of articulation bands, wherein the articulation bands are operable to simultaneously translate in opposing longitudinal directions relative to the shaft, wherein the articulation bands are further configured to both flare inwardly or both flare outwardly relative to a longitudinal axis of the shaft while simultaneously translating in opposing longitudinal directions, such that at least a portion of each articulation band is configured to move in a symmetrically opposing transverse motion relative to the longitudinal axis of the shaft while the articulation bands translate in opposing longitudinal directions.

19. The apparatus of claim 18, wherein each articulation band is configured to translate within the shaft, wherein each articulation band is operable to pivot the end effector relative to the shaft.

20. The apparatus of claim 18, wherein the shaft further comprises a first outer diameter, a second outer diameter, wherein the second outer diameter is proximal to the first outer diameter, wherein the second outer diameter is smaller than the first outer diameter, wherein each articulation band extends through the first outer diameter and the second outer diameter, wherein the shaft comprises a third outer diameter proximal to the second outer diameter, wherein the third outer diameter is larger than the second outer diameter.

* * * * *